United States Patent [19]

Heikkilä et al.

[11] Patent Number: 4,514,680
[45] Date of Patent: Apr. 30, 1985

[54] FLAW DETECTION SYSTEM USING MICROWAVES

[75] Inventors: Sakari Heikkilä; Martti Tiuri, both of Espoo, Finland

[73] Assignee: A.Ahlstrom Osakeyhtio, Noormarkku, Finland

[21] Appl. No.: 461,697

[22] Filed: Jan. 28, 1983

[51] Int. Cl.³ ............................................. G01R 27/04
[52] U.S. Cl. ............................ 324/58.5 A; 324/58.5 R
[58] Field of Search ............ 324/58.5 A, 58 A, 58.5 R

[56] References Cited

U.S. PATENT DOCUMENTS 3,810,005  7/1974  Bennion .
3,826,978  7/1974  Kelly ............................ 324/58.5 A
3,956,695  5/1976  Stamm ........................ 324/58.5 A
4,123,702  10/1978  Kinanen .

FOREIGN PATENT DOCUMENTS 2712600  9/1977  Fed. Rep. of Germany ...324/58.5 R

Primary Examiner—Stanley T. Krawczewicz
Assistant Examiner—Jose M. Solis
Attorney, Agent, or Firm—Bucknam and Archer

[57] ABSTRACT

A method and an apparatus for detection of flaws in lumber is provided, in which the lumber is subjected to microwave radiation of equal intensity in turns simultaneously from two microwave radiation means in phase opposition and from an intermediate microwave radiation means and between the turns from none of said microwave radiation means. The microwave radiation transmitted through the lumber is measured and the level of the measured signals in pulse form is adjusted in such a way that the mean value of the pulse train equals a reference value. The level of the pulse train when no radiation is transmitted is adjusted to zero and the level of the pulses when said two microwave radiation means in phase opposition radiate is used as a measure of the size of the flaw in the lumber.

6 Claims, 4 Drawing Figures

FLAW DETECTION SYSTEM USING MICROWAVES

The invention relates generally to systems for the detection of flaws in non-conducting materials such as e.g. lumber. Defects in lumber, for instance knots, can be readily detected using a microwave technique. The knot brings about change in the radiation passing through compared with the equivalent value measured in a knot-free area of the same lumber.

The method of the present invention is based on the use of two microwave transmitting means which are positioned to transmit radiation of equal field intensity, but with a phase shift of 180° between them, to one side of the lumber. In case of knot-free lumber there is a null in the microwave field pattern at the location of the receiving detectors and the detector output voltages are zero. A knot in the microwave field will disturb the phase and amplitude relationships at the knot detectors shaded by the knots. The signal generated by the detector is proportional to the size of the knot (amount of knot wood) in front of the detector.

Of some relevance to the present invention is U.S. Ser. No. 383,588, filed June 1, 1982, entitled: "Method and Apparatus for Detecting Grain Direction in Wood, Particularly in Lumber", as a continuation-in-part application of U.S. Ser. No. 042,517, filed May 25, 1979, entitled: "An Apparatus for Detecting Grain Direction in Timber, Etc.", which parent application is now abandoned. These applications were filed by a different applicant, but were assigned to the same Assignee as the present application.

These applications differ fundamentally from the present application in that they make use of polarizers for polarizing the waves from the transmitting antennas and then transmitting the radiation energy of the transmitting antennas through lumber whereby the dielectric anisotropy of the wood induces a change in the direction of the polarization, and the grain direction can then be calculated by obtaining signals based on the polarization change. On the other hand, the present invention is not concerned with detecting grain direction in lumber, but rather is concerned with detecting flaws such as knots in lumber. It does not make use of any polarization of transmitting antenna signals, but rather detects flaws by measurement of error signals generated by a plurality of signals transmitted through the wood.

The measurement of the microwave radiation passed through the lumber is affected by the variations of the attenuation of the radiation depending on the moisture content, density, temperature and thickness of the lumber. Also fluctuation of the transmitted power of the microwave source and variation of the sensitivity of the microwave detector means causes changes of the measured signal. Spatial radiation intensity variations in the measurement field pattern affect the accuracy of measurement as well.

It is an object of the present invention to provide a knot measuring system which is self-calibrating and therefore unaffected by the above mentioned variations.

The method and apparatus of the present invention include the use of three microwave transmitting means positioned in the line of motion of the lumber. The outer and the intermediate transmitting means, which is used to produce a reference signal, are activated alternatively.

The knot measuring system has an automatic gain control arrangement. To generate the gain control signal, the microwave power is applied to the centre transmitting means, causing a maximum of the field pattern to occur at the receiving detectors. The gain of the control circuit adjusts itself to such a value that the detector voltage is amplified to equal an internal stabilized reference voltage.

Between the transmitting pulses, there is a pause when the microwave radiation from both the outer and the centre transmitting means is blocked off. During this time, the electronic circuit operating by the synchronous detection principle restores the signal levels to zero.

Further objects and features of the present invention will become apparent from the following description which is made with reference to the accompanying drawings in which.

Figure 1:
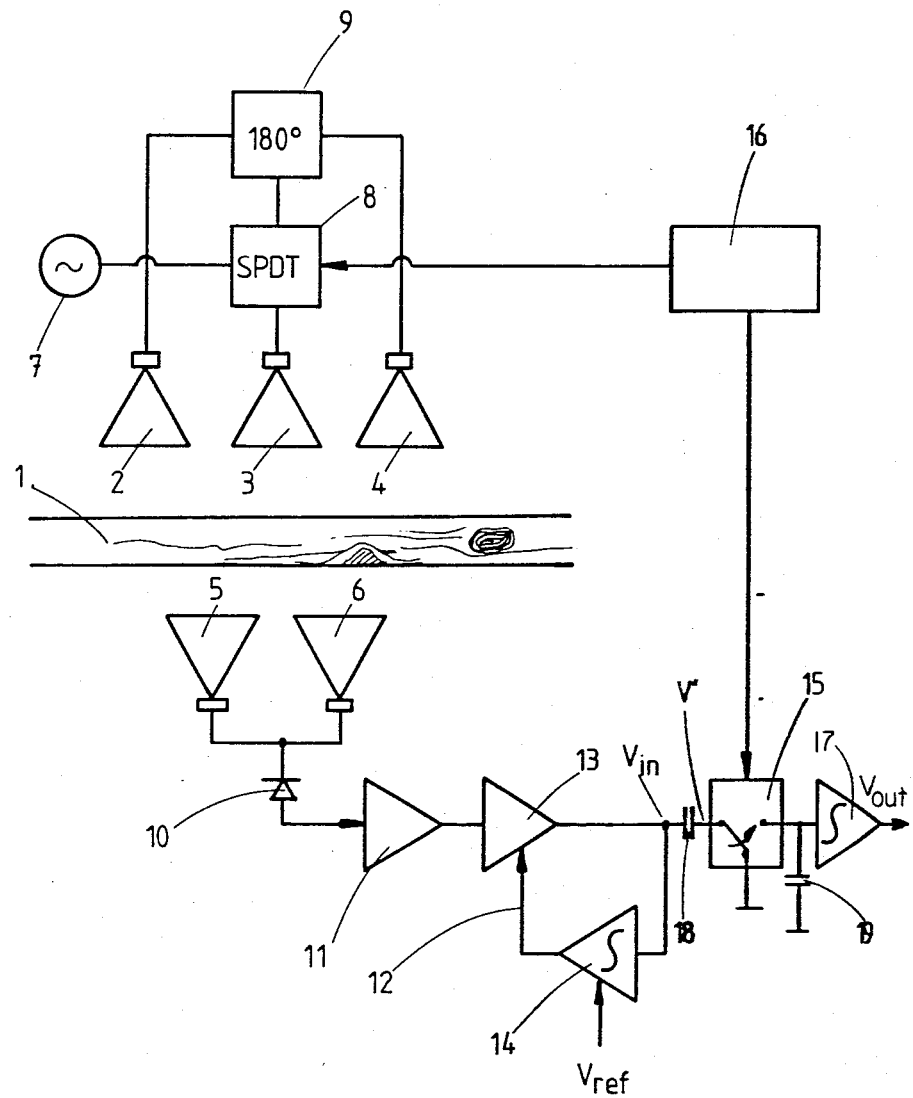
FIG. 1 is a block diagram of a flaw detection system embodying the invention.

As illustrated in FIG. 1, a piece of lumber 1 being examined by the detection of flaws, such as for instance knots, is passed in the line of motion of the lumber between three microwave transmitters 2, 3 and 4 and to receiving microwave aerials 5 and 6. A microwave oscillator 7 is connected to the intermediate microwave transmitting aerial 3 through a SPDT (single pole, double throw) switch 8 and to the other microwave transmitting aerials 2 and 4 through the SPDT switch and a T-junction 9 which causes the radiation fields produced by the aerials 2 and 4 to be opposite in phase. The radiation field of all transmitter aerials passed through the lumber is received by the receiving aerials 5 and 6. The intermediate transmitting aerial and the receiving aerials are preferably located symmetrically in respect of the outer transmitting aerials. The received radiation is measured by means of a detector 10 midway in the waveguide connecting the receiving aerials. The detector which is a conventional microwave detector diode is connected to a preamplifier 11. The circuit includes a loop 12 comprising an automatic gain control amplifier 13 and an integrator 14. By means of the automatic gain control, the level of the signal in pulse form from the detector is amplified in such a way that the mean value of the pulse train equals an internal stabilized reference value $V_{ref}$. The integrator 14 transforms the signals to a direct current which controls the gain of the amplifier 13. A zero set and sampling switch 15 controlled by a control unit 16 which also controls the SPDT switch 8 couples the signals originating from the outer transmitter aerials 2 and 4 from the automatic gain controller 13 to the integrator 17. The base level of the pulse train from the automatic gain control amplifier 13 corresponding to microwave radiation from none of the aerials 2, 3 and 4 is clamped to the ground level by means of the switch 15. When the control unit 16 switches off both ports of the SPDT switch 8, i.e. when none of the aerials 2, 3 and 4 are radiating and when synchronously the switch 15 is in zero set position, i.e. connected to the ground, a capacitor 18 disposed before the switch will become charged to the value $V_{in}$ and V', the voltage after the capacitor has the value $^0V$. When the switch 15 is switched to the sampling position, V' will start to follow the changes of $V_{in}$. During the sampling period the aerials 2 and 4 radiate and a capacitor 19 disposed after the switch will become charged to a voltage prevailing at the time of the sampling. When the switch 15 is in zero set position, the capacitor 19 will maintain this voltage until a new sample will change the situation. Sampling and automatic calibration of the measurement data are repeated e.g. 20,000 times per second.

The intensity of the radiation transmitted to the lumber from the outer microwave transmitting aerials 2 and 4 is equal. In case of a knot-free lumber, the radiation passing through the lumber and received by the receiving aerials, being opposite in phase, cancel each other at the detector 10. Zero output is then obtained from the detector 10. A knot in the radiation field between the transmitting aerial 4 and the receiving aerial 6 or between the transmitting aerial 2 and the receiving aerial 5 will cause a change of the phase difference and the detector 10 will produce a signal which is proportional to the size of the knot.

Figure 2:
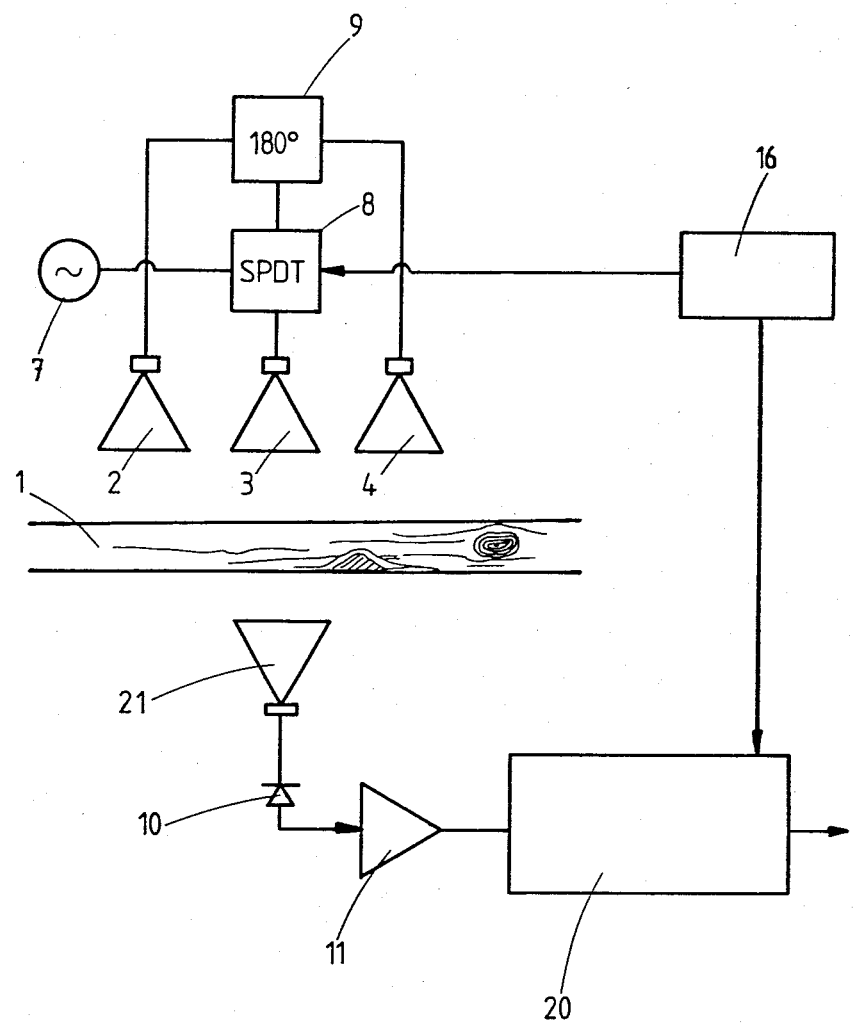
FIG. 2 is another embodiment of the invention.

In the embodiment of the invention disclosed in FIG. 2, parts corresponding with parts shown in FIG. 1 have been marked with the same reference numerals.

In operation, the embodiment of FIG. 2 operates in the same way as the system shown in FIG. 1, except that the loop 12, the switch 15 and the integrator 17 of FIG. 1 are substituted by a signal processor 20 which (a) performs an A/D conversion (analog to digital) of the signals, alternately for $V_\Delta$ which is the voltage of the output signal from the microwave detector when the aerials 2 and 4 radiate and for $V_\Sigma$ when the aerial 3 radiates, (b) stores the conversion results, (c) computes $V_{66}/(V_\Delta + V_\Sigma)$ The control unit 16 transmits to the signal processor information about the state of the SPDT switch 8.

The two receiving aerials 5 and 6 of FIG. 1 are substituted by one microwave receiving aerial 21.

Figure 3:
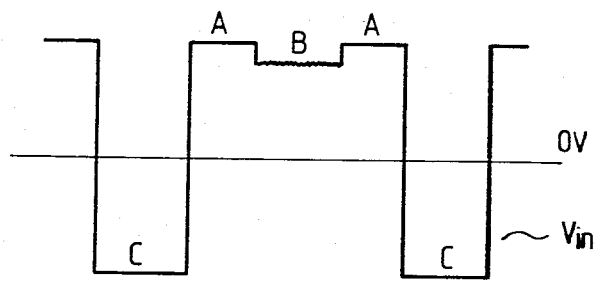
FIGS. 3 and 4 are graphic representations of a signal produced in the system.
Figure 4:
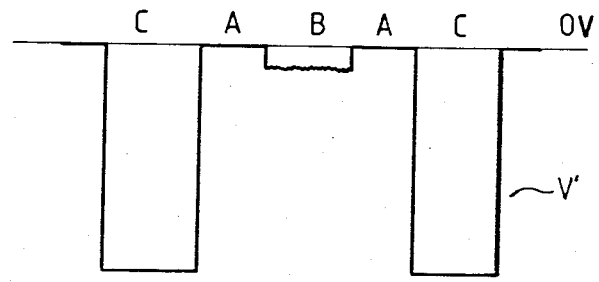

FIGS. 3 and 4 show how the output signal from the automatic gain control amplifier in the embodiment of FIG. 1 varies. $V_{in}$ in FIG. 3 is the voltage before the capacitor 18 and V' in FIG. 4 is the voltage after the capacitor. At A none of the aerials 2, 3 and 4 radiate. At B the aerials 2 and 4 radiate. At C the aerial 3 radiates.

While some specific embodiments of the invention has been described in detail above, it is to be understood that various modifications may be made from the specific details described without departing from the spirit and scope of the invention.

We claim:

1. Apparatus for detecting knots in lumber moving in relation to said apparatus, comprising:

first and second transmitting aerials positioned to transmit microwave radiation with 180° phase shift between them to one side of the lumber, a third transmitting aerial disposed between and in line with the first and the second transmitting aerials, a control unit for connecting a microwave generator at regular intervals simultaneously to both of the first and second aerials and to the third transmitting aerial at different intervals with the same regularity and between the transmission intervals to none of said transmitting aerials.

at least one receiving aerial positioned to receive the radiation passed through the lumber, a detector for measuring the received radiation, a loop containing an automatic gain control amplifier and an integrator for adjusting the level of the signals from said detector in such a way that the mean value of the signals equals an interval stabilized reference value, and a zero set and sampling switch controlled by said control unit for causing only the signals originating from the first and second transmitter aerials to pass through and in its zero position when no aerial is radiating to restore the signal level to zero.

2. Apparatus as defined in claim 1 further comprising an integrator transforming the signals from said zero set and sampling switch to a direct current voltage signal which is used as a measure of the size of the knot in front of said receiving aerials.

3. Apparatus as defined in claim 1, wherein there are two microwave receiving aerials.

4. Apparatus for detecting knots in lumber moving in relation to said apparatus, comprising:

first and second transmitting aerials positioned to transmit microwave radiation with 180 phase shift between them to one side of the lumber, a third transmitting aerial disposed between and in line with the first and the second transmitting aerials, a control unit for connecting a microwave generator at regular intervals simultaneously to both of the first and second aerials and at different intervals with the same regularity to the third transmitting aerial and between the transmission intervals to none of said transmitting aerials, at least one receiving aerial positioned to receive the radiation passed through the lumber, a detector for measuring the received radiation, a preamplifier to amplify the signal from said detector, a signal processor comprising:

(a) means for performing an A/D conversion of the signals from said preamplifier, alternatively for $V_\Delta$ which is the voltage of the signal when said first and second transmitting aerials radiate and for $V_\Sigma$ which is the voltage of the signals when said third transmitting aerial radiates, (b) means for storing the results of said A/D conversion, (c) means for computing $V_{66}/(V_\Delta + V_\Sigma)$ 5. A method for detection of flaws in non-conducting material, comprising the steps of:

transmitting microwave radiation of equal intensity to the material at regular intervals simultaneously from two microwave radiation means in phase opposition and at different intervals with the same regularity from an intermediate microwave radiation means and between the transmission intervals from none of said microwave radiation means, receiving microwave radiation transmitted through and attenuated by the material at least at one microwave detecting means, measuring the voltage $V_\Delta$ of the output signal from said microwave detecting means when said two microwave radiation means simultaneously radiate, measuring the voltage $V_\Sigma$ of the output signal from said microwave detecting means when said intermediate microwave radiation means only radiate, and forming the quantity $V_\Delta/V_\Delta + V_\Sigma$ the magnitude of which is proportional to the size of the flaw in front of said microwave detecting means.

6. A method for detection of flaws in non-conducting material having at least one widely varying physical characteristic affecting the attenuation of microwave radiation transmitted through the material, comprising the steps of:

transmitting microwave radiation of equal intensity to the material at regular intervals simultaneously from two microwave radiation means in phase operation and from an intermediate microwave radiation means at different intervals with the same regularity and between the transmission intervals from none of said microwave radiation means, measuring the microwave radiation transmitted through the material, adjusting the level of the measured signals in such a way that the mean value signals equals a reference value, and adjusting the level of the measured signals when no radiation is transmitted to zero and using the level of the measured signals when said to microwave radiation means in phase opposition radiate as a measure of the size of the flaw in the material.

* * * * *

UNITED STATES PATENT AND TRADEMARK OFFICE
CERTIFICATE OF CORRECTION

PATENT NO. : 4,514,680
DATED : April 30, 1985
INVENTOR(S) : Sakari Heikkila, Martti Tiuri It is certified that error appears in the above-identified patent and that said Letters Patent are hereby corrected as shown below:

In column 3, line 32 -
"$V_{66}$" should read --$V_{\Delta}$--

In claim 4, line 43
"$V_{66}$" should read --$V_{\Delta}$--

Signed and Sealed this

Twenty-ninth Day of July 1986

[SEAL]

Attest:

Attesting Officer

DONALD J. QUIGG

Commissioner of Patents and Trademarks